United States Patent [19]
Errico et al.

[11] Patent Number: 5,817,094
[45] Date of Patent: Oct. 6, 1998

[54] POLYAXIAL LOCKING SCREW AND COUPLING ELEMENT

[75] Inventors: Joseph P. Errico, Far Hills; Thomas J. Errico, Summit; James D. Ralph, Oakland, all of N.J.

[73] Assignee: Fastenetix, LLC, Summit, N.J.

[21] Appl. No.: 788,804

[22] Filed: Jan. 23, 1997

Related U.S. Application Data

[63] Continuation of Ser. No. 559,196, Nov. 13, 1995, abandoned, which is a continuation-in-part of Ser. No. 421,087, Apr. 13, 1995, Pat. No. 5,520,690.

[51] Int. Cl.$^6$ .................................................. A61B 17/70
[52] U.S. Cl. .............................................. 606/61; 606/73
[58] Field of Search ................................. 606/61, 60, 72, 606/73, 69, 70, 71; 623/17

[56] References Cited

U.S. PATENT DOCUMENTS

| | | |
|---|---|---|
| 3,779,240 | 12/1973 | Kondo . |
| 4,493,317 | 1/1985 | Klaue . |
| 4,946,458 | 8/1990 | Harms et al. . |
| 5,053,036 | 10/1991 | Perren et al. . |
| 5,057,111 | 10/1991 | Park . |
| 5,147,361 | 9/1992 | Ojima et al. . |
| 5,151,103 | 9/1992 | Tepic et al. ................................ 606/69 |
| 5,180,381 | 1/1993 | Aust et al. . |
| 5,207,678 | 5/1993 | Harms et al. . |
| 5,269,784 | 12/1993 | Mast . |
| 5,324,290 | 6/1994 | Zdeblick et al. . |
| 5,360,431 | 11/1994 | Puno et al. ................................ 606/72 |
| 5,395,371 | 3/1995 | Miller et al. . |
| 5,429,639 | 7/1995 | Judet . |
| 5,443,467 | 8/1995 | Biedermann et al. ..................... 606/65 |
| 5,476,464 | 12/1995 | Metz-Stavenhagen et al. . |
| 5,480,401 | 1/1996 | Navas . |

FOREIGN PATENT DOCUMENTS

WO 94/16634  8/1994  WIPO .

OTHER PUBLICATIONS

"Cervi–Lok Cervical Fixation System", Spinetech, Inc., 980 E. Hennepin Ave., Minneapolis, Minn. 55414, 1994.

System Overview–Axis Fixation System, Sofamor Danek, 1800 Pyramid Place, Memphis, TN 38132, 1994.

"Surgical Technique–Orion Anterior Cervical Plate System", Sofamor Danek, 1800 Pyramid Place, Memphis, TN 38132, 1994.

"Surgical Technique–ZPlate–ATL Anterior Fixation System", Sofamor Danek, 1800 Pyramid Place, Memphis, TN 38132, 1994.

*Primary Examiner*—Guy V. Tucker
*Attorney, Agent, or Firm*—Joseph P. Errico, Esq.

[57] ABSTRACT

A polyaxial orthopedic device for use with rod implant apparatus includes a screw having a curvate head, a locking collar disposed therearound, and a coupling element having a tapered socket into which both the screw and the collar are securely nested. The locking collar is slotted and tapered, and has a semi-spherical interior volume into which the screw head is initially polyaxially held. The coupling element has an axial bore through which the screw and locking collar may be inserted, and a tapered bottom which provides a radially inward force on the locking collar when forces thereinto. This radially inward force causes the locking collar to crush lock against the head of the screw, therein locking the two at the instant angulation. In an initial disposition, however, the screw head remains polyaxially free with respect to the locking collar, and with the coupling element. The coupling element includes a transverse channel in which a rod may be disposed. In a first embodiment the channel is formed between a pair of upwardly extending members, and in a second embodiment, the channel is formed in the side of the element. In either case, a rod which is inserted in the channel, seats against the top of the locking ring.

10 Claims, 9 Drawing Sheets

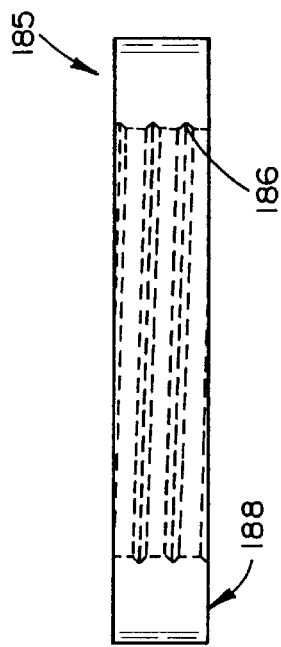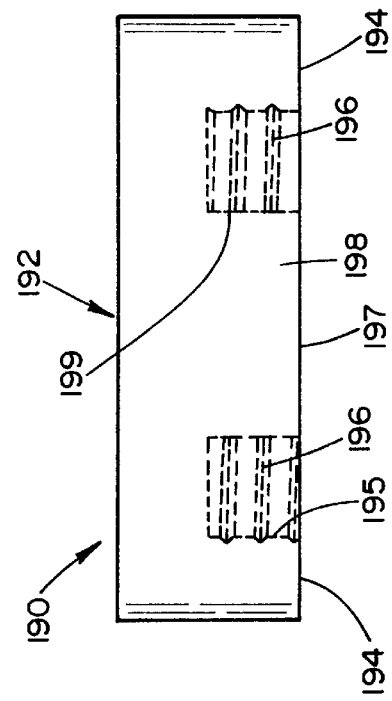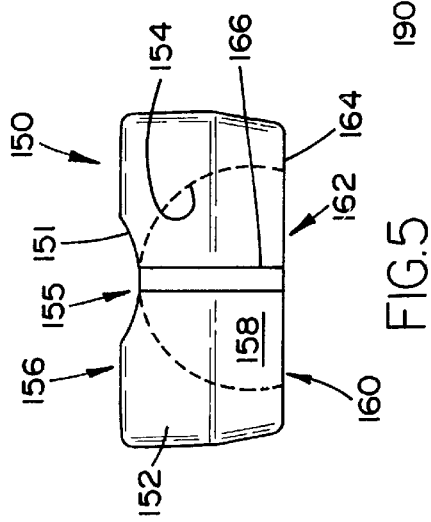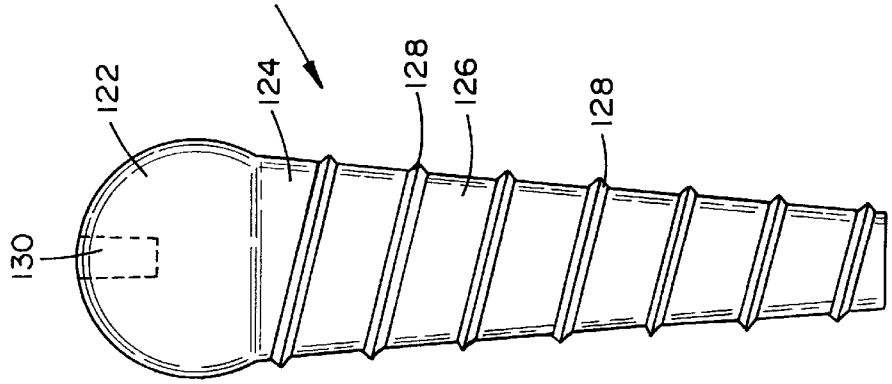

POLYAXIAL LOCKING SCREW AND COUPLING ELEMENT

CROSS-REFERENCE TO PRIOR APPLICATION

This application is a continuation of application Ser. No. 08/559,196, filed Nov. 13, 1995, (now abandoned), which is a continuation-in-part of application Ser. No. 08/421,087, filed Apr. 13, 1995, now U.S. Pat. No. 5,520,690.

BACKGROUND OF THE INVENTION

1. Field of the Invention

This invention relates generally to a polyaxial screw and coupling apparatus for use with orthopedic fixation systems. More particularly, the present invention relates to a screw for insertion into spinal bone, and a coupling element polyaxially mounted thereto, via a slotted taper ring, for coupling the screw to an orthopedic implantation structure, such as a rod, therein enhancing the efficacy of the implant assembly by providing freedom of angulation among the rod, screw and coupling element.

2. Description of the Prior Art

The bones and connective tissue of an adult human spinal column consist of more than 20 discrete bones coupled sequentially to one another by a tri-joint complex which consist of an anterior disc and the two posterior facet joints, the anterior discs of adjacent bones being cushioned by cartilage spacers referred to as intervertebral discs. These more than 20 bones are anatomically categorized as being members of one of four classifications: cervical, thoracic, lumbar, or sacral. The cervical portion of the spine, which comprises the top of the spine, up to the base of the skull, includes the first 7 vertebrae. The intermediate 12 bones are the thoracic vertebrae, and connect to the lower spine comprising the 5 lumbar vertebrae. The base of the spine is the sacral bones (including the coccyx). The component bones of the cervical spine are generally smaller than those of the thoracic and lumbar spine. For the purposes of this disclosure, however, the word spine shall refer only to the cervical region.

Referring now to FIGS. 1, 2, and 3, top, side, and posterior views of a vertebral body, a pair of adjacent vertebral bodies, and a sequence of vertebral bodies are shown, respectively. The spinal cord is housed in the central canal 10, protected from the posterior side by a shell of bone called the lamina 12. The lamina 12 includes a rearwardly and downwardly extending portion called the spinous process 16, and laterally extending structures which are referred to as the transverse processes 14. The anterior portion of the spine comprises a set of generally cylindrically shaped bones which are stacked one on top of the other. These portions of the vertebrae are referred to as the vertebral bodies 20, and are each separated from the other by the intervertebral discs 22. The pedicles 24 comprise bone bridges which couple the anterior vertebral body 20 to the corresponding lamina 12.

The spinal column of bones is highly complex in that it includes over twenty bones coupled to one another, housing and protecting critical elements of the nervous system having innumerable peripheral nerves and circulatory bodies in close proximity. In spite of these complexities, the spine is a highly flexible structure, capable of a high degree of curvature and twist in nearly every direction. Genetic or developmental irregularities, trauma, chronic stress, tumors, and disease, however, can result in spinal pathologies which either limit this range of motion, or which threaten the critical elements of the nervous system housed within the spinal column. A variety of systems have been disclosed in the art which achieve this immobilization by implanting artificial assemblies in or on the spinal column. These assemblies may be classified as anterior, posterior, or lateral implants. As the classifications suggest, lateral and anterior assemblies are coupled to the anterior portion of the spine, which is the sequence of vertebral bodies. Posterior implants generally comprise pairs of rods, which are aligned along the axis which the bones are to be disposed, and which are then attached to the spinal column by either hooks which couple to the lamina or attach to the transverse processes, or by screws which are inserted through the pedicles.

"Rod assemblies" generally comprise a plurality of such screws which are implanted through the posterior lateral surfaces of the laminae, through the pedicles, and into their respective vertebral bodies. The screws are provided with upper portions which comprise coupling elements, for receiving and securing an elongate rod therethrough. The rod extends along the axis of the spine, coupling to the plurality of screws via their coupling elements. The rigidity of the rod may be utilized to align the spine in conformance with a more desired shape.

It has been identified, however, that a considerable difficulty is associated with inserting screws along a misaligned curvature and simultaneously exactly positioning the coupling elements such that the rod receiving portions thereof are aligned so that the rod can be passed therethrough without distorting the screws. Attempts at achieving proper alignment with fixed screws is understood to require increased operating time, which is known to enhance many complications associated with surgery. Often surgical efforts with such fixed axes devices cannot be achieved, thereby rendering such instrumentation attempts entirely unsucessful.

The art contains a variety of attempts at providing instrumentation which permit a limited freedom with respect to angulation of the screw and the coupling element. These teachings, however, are generally complex, inadequately reliable, and lack long-term durability. These considerable drawbacks associated with prior art systems also include difficulty properly positioned the rod and coupling elements, and the tedious manipulation of the many small parts in the operative environment.

It is, therefore, the principal object of the present invention to provide a pedicle screw and coupling element assembly which provides a polyaxial freedom of implantation angulation with respect to rod reception.

In addition, it is an object of the present invention to provide such an assembly which comprises a reduced number of elements, and which correspondingly provides for expeditious implantation.

Accordingly it is also an object of the present invention to provide an assembly which is reliable, durable, and provides long term fixation support.

Other objects of the present invention not explicitly stated will be set forth and will be more clearly understood in conjunction with the descriptions of the preferred embodiments disclosed hereafter.

SUMMARY OF THE INVENTION

The preceding objects of the invention are achieved by the present invention which is a polyaxial locking screw and coupling element for use with rod stabilization and immobilization systems in the spine. More particularly, the polyaxial screw and coupling element assembly of the present invention comprise a bone screw having a head which is curvate in shape, for example semi-spherical, a slotted and tapered locking collar, and a coupling element mounted thereto so as to be free to rotate prior to the secure fixation of the rod thereto, but which may be securely locked at a given angulation once the rod is received. The coupling element has an upper portion and a lower portion, the upper portion including a channel for receiving a rod therein, and the lower portion including a tapered socket for retaining and providing radial locking force against the slotted and tapered locking collar which in turn retains the head of the polyaxial screw. The coupling element further comprises an exterior threading thereon for receiving a top locking nut.

The locking collar comprises a short hollow cylindrical section, having a very mild exterior taper and a semi-spherical interior surface. This interior surface is ideally suited for holding therein the semi-spherical head of the screw. The top of the locking collar is open so that a screwdriving tool, for example an allen wrench or threaded post, may be used in conjunction with a corresponding recess in the semi-spherical head of the screw to drive it into the desired vertebral bone. The locking collar also includes an axial slot, such that the application of a radially compressive force may thus narrow the slot and narrow the interior volume. Conversely, the application of a radially outward force causes the slot to expand and the interior volume to increase. In an unforced state, the head of the screw and the collar remain free to swing relative to one another, however, the application of a radially inward force causes the interior surface of the collar to contract against the head of the screw, thereby crush locking the two elements together.

The coupling element comprises a cylindrical body having a cylindrical bore extending axially therethrough. The diameter of the bore is sufficient to permit the screw, its head, and the locking collar mounted about the head to slide loosely from the top of the bore to the bottom. The bottom of the bore, however, tapers inward, to a diameter which is less than the loose (non-radially compressed) locking collar, such that when the locking collar is forced downward as far as it can be pushed, the collar is radially compressed so that the head of the screw can be locked to it.

The rod receiving upper portion of the coupling element comprises a channel wherein the rod of the implant apparatus is mounted. More particularly, the walls of the hollow cylindrical body include opposing vertically oriented slots which extend downward from the top of the element and which, therefore, which form a channel through the element. This channel divides the upper portion into two upwardly extending members, between which the rod receiving channel is disposed. The vertical slots have curvate bottom surfaces for receiving thereon the rod.

In its initial, unlocked position (prior to being forced downward to the bottom of the axial bore of the element), the top of the locking collar rests higher than the curvate bottoms of the slots, such that when the rod is placed in the channel, it seats against it and not the curved bottom channel.

The upper portion of the upwardly extending members of the element comprise an external surface threading onto which a locking nut may be disposed and translated downwardly. If a rod is disposed in the channel, the downward translation of the locking nut provides a corresponding downward force onto the rod. The downward force on the rod translates into a downward force on the locking collar causing it to be forced downward into the tapered bottom of the bore (or conversely, the translation of the nut on the external threading of the element draws the element upward while holding the locking collar in place). This relative motion of the locking collar into the tapered bottom of the bore causes the rod to seat against the curved bottom of the channel, the screw to be angularly locked in the locking collar, and the locking collar to be locked within the bottom of the element.

In a preferred variation, the locking nut comprises a cap nut which has a central post which is designed to provide additional structural support to the inner walls of the element at the top thereof, as well as providing a central seating pressure point for locking the rod in the channel. In either variation, the locking nut seats against the rod and prevents it from moving translationally, axially and rotationally.

The first step in the process of implanting this invention is to insert the head of the screw into the locking collar. This may be done prior to the surgery, such as by a surgical assistant, or even at the manufacturing site. The screw, and the collar, are then inserted through the axial bore of the coupling element, from the top, until the tapers of the bottom of the bore and the collar mutually engage. At this point, the screw remains rotationally free to angulate relative to the locking collar, and therefore, the coupling element.

Once the screw has been so positioned, the screw and the coupling element are aligned with respect to one another so that the appropriate screwdriving tool may be inserted down the axial bore, into the recess in the head of the screw, and used to rotate the bone screw into the bone.

Subsequent to the insertion of the screw, the screwdriving tool may be removed from the assembly (or, in the case of a threaded post, be left in for alignment purposes), and the coupling element is rotated to change angular alignment relative to the screw. Although the locking collar has not yet been driven downwardly into full locking engagement with the bottom of the axial bore, and correspondingly with the head of the screw, the locking collar is sufficiently constrained by the axial bore such that the collar and the coupling element mutually angulate relative to the screw. In fact, it is the angulation freedom of the locking collar which defines the range of angles through which the coupling element may be angulated.

The rod of the implantation apparatus is then provided into the rod receiving channel, and is positioned so that it seats against the top of the locking collar, which is slightly above the curvate bottom of the channel. The top locking nut is then introduced onto the threaded top portion of the upwardly extending members until the bottom of the nut (and a post, in the cap variation which includes a central post) seats against the top of the rod. Continued tightening of the top locking nut causes the coupling element to be drawn upward and/or the locking collar to be driven downward, so that the collar fully seats in the bottom of the axial bore. This causes the screw head to be crush locked within the locking collar and the collar within the coupling element.

Multiple screw and coupling element assemblies are generally necessary to complete the full array of anchoring sites for the rod immobilization system, however, the screw and coupling element assembly of the present invention is designed to be compatible with alternative rod systems so that, where necessary, the present invention may be employed to rectify the failures of other systems the implantation of which may have already begun. For example, it is contemplated that this invention may alternatively be embodied with a side channel, instead of a top channel, wherein the rod is received by the coupling element in its side. Such a variation may further require the use of a rod securing sleeve in conjunction with the top locking nut. Such a sleeve may comprise a hollow cylindrical body, having a curvate bottom surface for engaging a rod, and which fits over the top of the element to seat against the rod. The top locking nut of a side loading variation would engage the sleeve, and the sleeve would in turn engage the rod.

BRIEF DESCRIPTION OF THE FIGURES

FIG. 4 is a side view of a screw having a curvate head which is an aspect of the present invention.

FIG. 5 is a side view of the locking collar of present invention, wherein critical interior features of the element are shown in phantom.

FIGS. 7a and 7b are a side cross-sectional views of top locking nuts which are aspects of the present invention; wherein FIG. 7a shows a simple open nut, and wherein FIG. 7b shows a cap nut having a central post.

DETAILED DESCRIPTION OF THE PREFERRED EMBODIMENT

Figure 2:
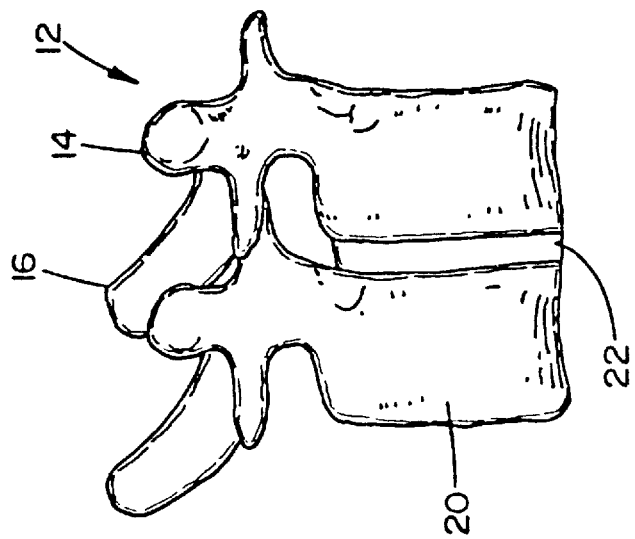
FIG. 2 is a side view of a pair of adjacent vertebrae of the type shown in FIG. 1.
Figure 1:
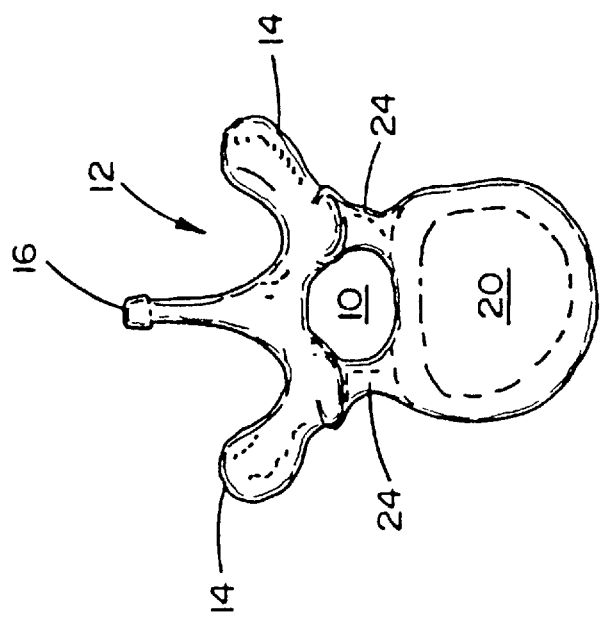
FIG. 1 is a top view of a human vertebra, which is representative of the type for which the present invention is useful for coupling thereto a rod apparatus.
Figure 3:
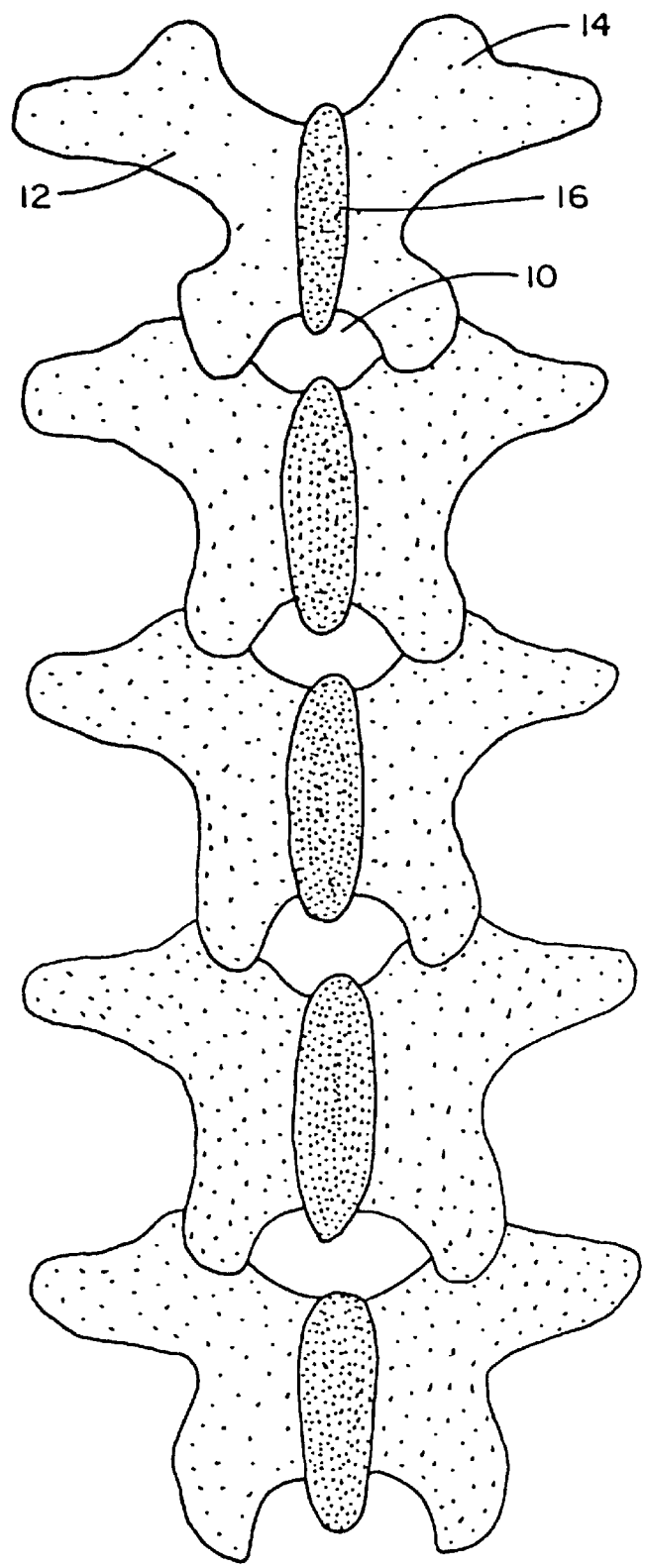
FIG. 3 is a posterior view of a sequence of vertebrae of the type shown in FIGS. 1 and 2.

While the present invention will be described more fully hereinafter with reference to the accompanying drawings, in which particular embodiments and methods of implantation are shown, it is to be understood at the outset that persons skilled in the art may modify the invention herein described while achieving the functions and results of this invention. Accordingly, the descriptions which follow are to be understood as illustrative and exemplary of specific structures, aspects and features within the broad scope of the present invention and not as limiting of such broad scope.

Referring now to FIG. 4, a side view of the screw portion of the present invention, comprising a curvate head, is shown. The screw 120 comprises a head portion 122, a neck 124, and a shaft 126. In FIG. 4, the shaft 126 is shown as having a tapered shape with a high pitch thread 128. It shall be understood that a variety of shaft designs are interchangeable with the present design. The specific choice of shaft features, such as thread pitch, shaft diameter to thread diameter ratio, and overall shaft shape, should be made be the physician with respect to the conditions of the individual patient's bone, however, this invention is compatible with a wide variety of shaft designs.

The head portion 122 of the screw 120 comprises a semi-spherical shape, which has a recess 130 in it. It is understood that the semi-spherical shape is a section of a sphere, in the embodiment shown the section is greater in extent than a hemisphere, and it correspondingly exhibits an external contour which is equidistant from a center point of the head. In a preferred embodiment, the major cross-section of the semi-spherical head 122 (as shown in the two dimensional illustration of FIG. 4) includes at least 270 degrees of a circle.

The recess 130 defines a receiving locus for the application of a torque for driving the screw 120 into the bone. The specific shape of the recess 122 may be chosen to cooperate with any suitable screw-driving tool. For example, the recess 130 may comprise a slot for a screwdriver, a hexagonally shaped hole for receiving an allen wrench, or most preferably, a threading for a correspondingly threaded post. It is further preferable that the recess 130 be co-axial with the general elongate axis of the screw 120, and most particularly with respect to the shaft 126. Having the axes of the recess 130 and the shaft 126 co-linear facilitates step of inserting the screw 120 into the bone.

The semi-spherical head portion 122 is connected to the shaft 126 at a neck portion 124. While it is preferable that the diameter of the shaft 126 be less than the diameter of the semi-spherical head 122, it is also preferable that the neck 124 of the screw 120 be narrower than the widest portion of the shaft 126. This preferable dimension permits the screw to swing through a variety of angles while still being securely joined to the locking collar (as set forth more fully with respect to FIGS. 5, 8–9, and 12).

Referring now to FIG. 5, the locking collar of the present invention is shown in a side view, wherein phantom lines show the interior structure of the elements along a diametrical cross section. The locking collar 150 comprises a slotted and tapered cylindrical body 152 having a semi-spherical interior surface 154. The top surface 156 of the locking collar 150 has an opening 155 through which the screw-driving tool which is used to insert the screw 120 into the bone may access and rotate the screw 120 through the collar 150. In addition, the top surface 156 of the collar 150 may also comprise a pair of opposing notches 151 which are curvate and ideally suited for the rod 250 to seat thereon.

The interior semi-spherical volume 158 is ideally suited for holding the head portion 122 of the screw 120, and permitting the screw to rotate through a range of angles. The bottom 160 of the locking collar 150 has a circular hole 162, defined by annular lip 164, which forms the bottom entrance into the interior semi-spherical volume 158. It is understood that the head 122 of the screw 120 is held within the interior semi-spherical volume 158 by the relative size of the head 122 as compared with the openings 155 and 162. More specifically, the annular lip 164 defines the circular opening 162 which has a diameter less than the diameter of the semi-spherical head 122 of the screw 120.

In order that the head 122 of the screw 120 may be inserted into the locking collar 150, the collar is slotted, preferably with a single axial slot 166, extending the entire length of the collar, thus rendering the collar an incomplete circle. This permits the collar 150 to be opened or closed, narrowed or expanded, in accordance with the application of radial forces directed thereto. (It is understood that a series of slots in the lower portion of the collar 150 may similarly permit expansion and narrowing of the interior volume 158, however, the single slot 166 design is preferable it provides for nearly equal expansion and contraction of the entire interior surface 154 of the collar 150 upon the application of a radial force.) The slot 166 permits the head portion 122 to be inserted into the interior volume 158 of the locking collar 150, so that while being rotationally free to move once disposed therein, the head 122 may not be easily removed.

Figure 6:
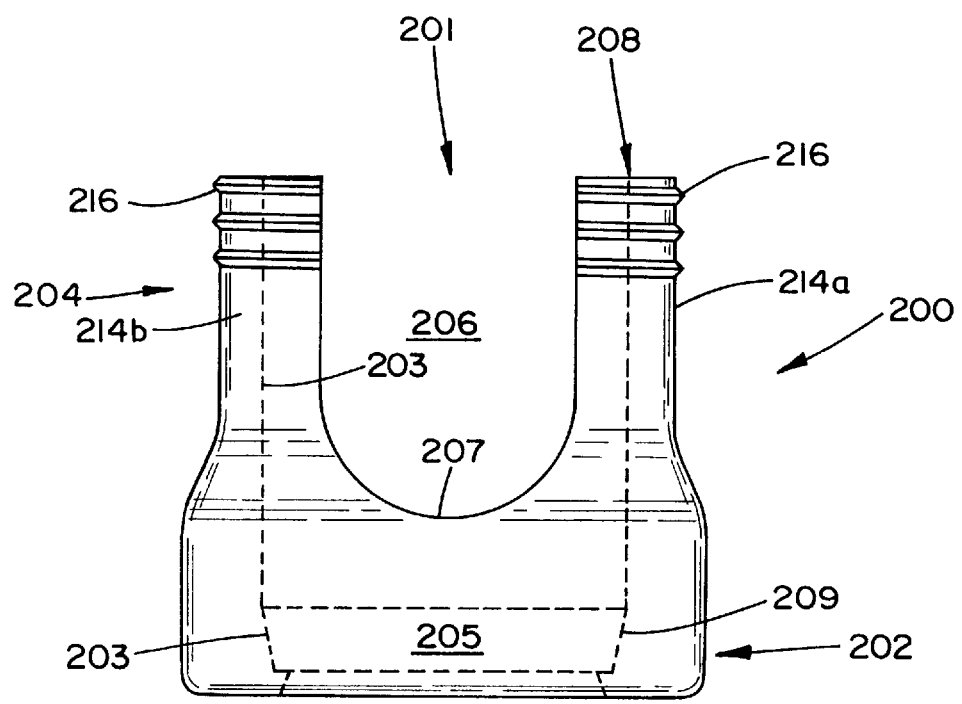
FIG. 6 is a side view of a first coupling element of the present invention wherein interior features of the element are shown in phantom.

Referring now to FIG. 6, the coupling element 200 of the present invention is shown in a side view, wherein critical features of the interior of the element are shown in phantom. The coupling element 200, which comprises a generally cylindrical tubular body having an axial bore 201 extending therethrough, may be conceptually separated into a lower portion 202, and an upper portion 204, each of which shall be described more fully hereinbelow.

First, with respect to the lower portion 202, the interior surface 203 of the axial bore 201 has an inward taper 209 at the bottom thereof. The diameter of the remainder of the axial bore 201 is such that the screw 120 and the locking collar 150 may be inserted therethrough without applying a radially inward force against the collar 150. The inwardly tapered region at the bottom of the axial bore, however, defines a socket 205, into which the locking collar 150 and the head 122 of the screw 120 disposed therein may nest. Prior to its being fully driven into the socket 205, the screw 120 may be angulated relative to the coupling element 200, and the locking collar 150. Once driven fully into the socket 205, however, the taper of the interior surface 203 of the axial bore 201 provides the necessary inwardly directed radial force to cause the locking collar 150 to crush lock to the head 122 of the screw 120.

The upper portion 204 of the coupling element 200 includes a pair of opposing, vertically oriented, slots 206 (one of which is shown in FIG. 6) having rounded bottom surfaces 207. These slots 206 form a rod receiving channel descending downward from the top 208 of the coupling element 200. The channel, in turn, divides the wall cylindrical body of the upper portion 204 into a pair of upwardly extending members 214a,214b. As shown in the embodiment illustrated in FIG. 6, the vertical distance from the top 208 of the channel to the curvate bottom 207 thereof, is larger than the diameter of the rod which is to be provided therein. This distance is necessarily larger than the diameter of the rod (see FIG. 9) so that the rod may be fully nested in the channel. In addition, the depth of the bottom curvate surface 207 of the channel is such that the top of the locking collar 150 is thereabove, prior to its full nesting into the socket 205.

The top 208 of the upper portion 204, which comprises upwardly extending members 214a,214b, have disposed thereon a threading 216. This threading 216 thereon, is ideally suited for receiving a top locking nut (see FIGS. 7a and 7b).

Referring now to FIGS. 7a and 7b, a pair of alternative top locking nuts are shown in side cross-section view. First with respect to FIG. 7a, the nut 185 comprises an inner threading 186 which is intended to mate with the threading 216 on the upwardly extending members 214a,214b of the upper portion 204 of the coupling element 200. The bottom surface 188 of the nut 185 is intended to seat against the top surface of the rod 250, but is permitted to rotate relative thereto, therein providing a means for driving the rod downward (as more fully described hereinbelow with respect to the full assembly of the device, and with respect to FIG. 9).

With respect to the variation of the top locking nut of FIG. 7b, the locking nut may further comprise a cap nut 190 having a central post 190. In such a design, the nut includes a circular top portion 192, having an annular flange portion 194 extending downwardly therefrom at the periphery thereof. The interior surface 196 of this flange portion 194 comprises a threading 195 which is designed to engage the threading 216 of the upwardly extending members 214a, 214b. A cylindrical post 198 is positioned at the center of the undersurface of the circular portion 192, such that the distance between the exterior surface 199 of the central post 198 and the inner threaded surface 196 of the flange portion 194 is sufficient for the upwardly extending members 214a, 214b, on which the threadings 216 are disposed, to be engaged by the cap nut. Once fully engaged, the central post 198 provides enhanced strength to the upwardly extending members 214a, 214b, so that they will not bend inwardly, toward one another, thus weakening the top locking nut's holding ability. In addition, if the central post is sufficiently long, the bottom 197 thereof may be used to seat against the rod 250 (see FIG. 9) to enhance the locking thereof to the coupling element 200.

Figure 8:
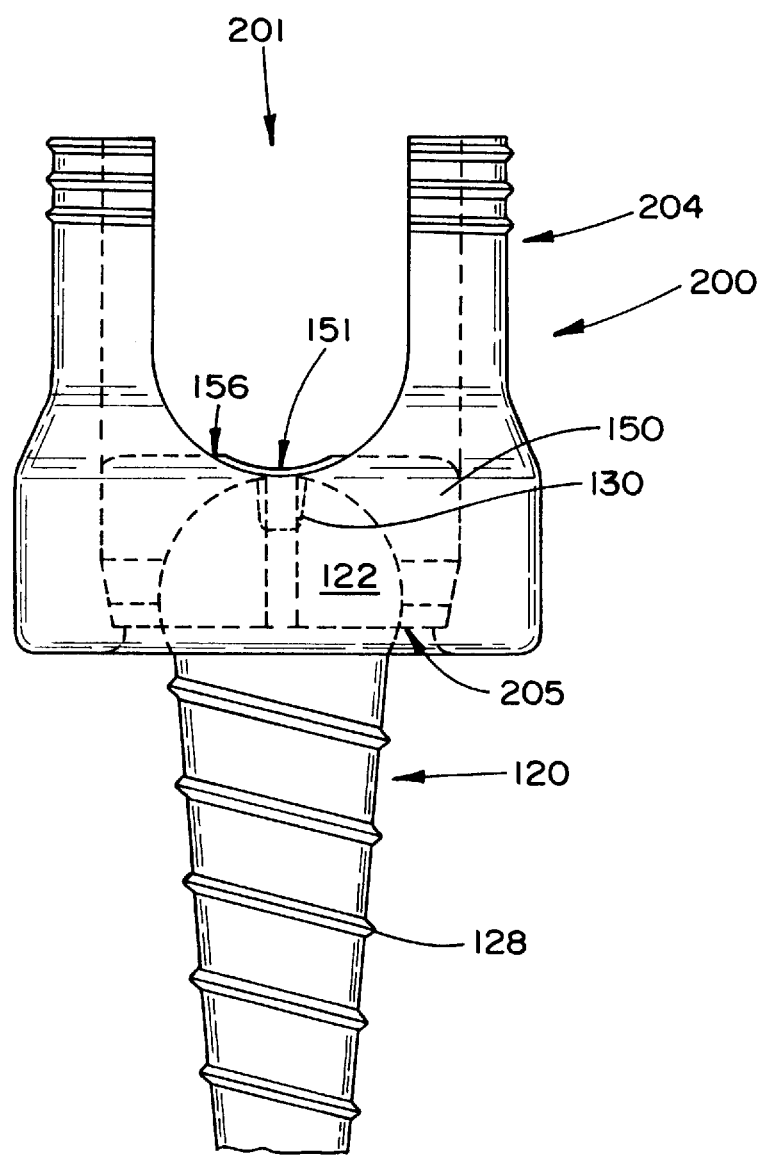
FIG. 8 is a side cross-sectional view of a first embodiment of the present invention in its semi-assembled disposition having the screw and locking collar disposed in the coupling element.
Figure 9:
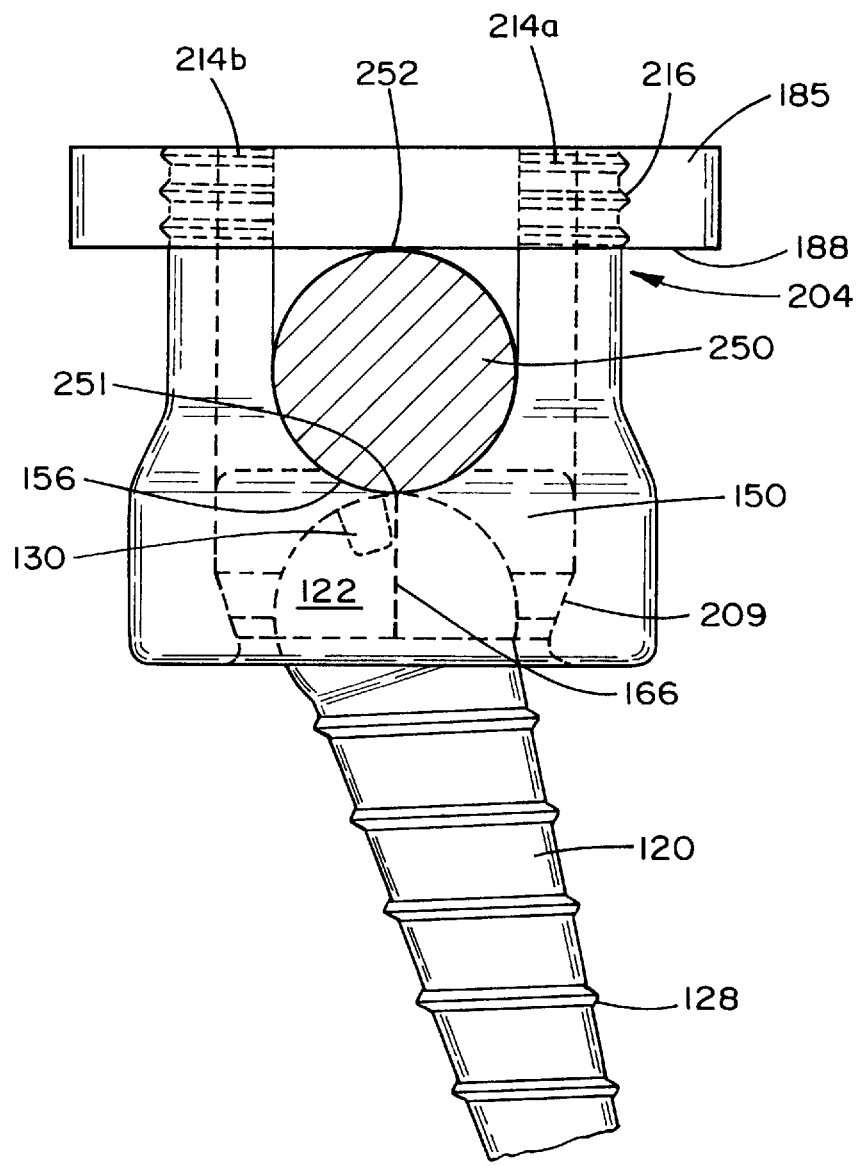
FIG. 9 is a side cross-sectional view of the first embodiment of the present invention in its fully assembled disposition having a rod securely locked therein.

Referring now to FIGS. 8 and 9, which show side views of the initial disposition of the screw, collar, and coupling element, and the fully locked coupling element, rod, collar and screw system, respectively, the preferred method of implantation and assembly is described hereinbelow. First, a pre-drilled hole is provided in the bone, into which it is desired that the screw 120 be disposed. The hole may be pre-tapped, or the external threading 128 of the screw 120 may include a self-tapping lead edge. In either event, the head 122 of the screw 120 is inserted into the locking collar 150, such that it remains polyaxially free to rotate and angulate relative thereto. The locking collar 150 and the screw 120 are then translated downward, through the axial bore 201 of the coupling element 200, until the locking collar 150 seats loosely in the socket 205 at the tapered bottom of the axial bore 201. At this point in the assembly process, the screw 120 and the locking collar 150 have the capacity to rotate relative to one another, while the loose seating of the locking collar in the socket 205 prevents relative motion of the collar and the element. In order to ensure that relative rotational motion of the locking collar and the coupling element is prevented, a portion of the axial extent of the locking collar may include a circumferential arc section which is flat, and a corresponding flat surface on the interior surface of the axial bore. The mutual engagement of the flat portions prevents the locking ring from rotating, but not from sliding axially within the axial bore. In the initial position, the top surface 156 of the locking collar 150 is disposed above the curvate bottom of the channel of the upper portion 204 of the coupling element 200, such that the notches 151 of the collar 150 are generally aligned with the channel.

By orienting the locking collar 150 and the screw 120 coaxially, a screwdriving tool may engage the recess 130 in the head 122 of the screw 120 so that it may be driven into the preformed hole in the bone.

Subsequent to the screw 120 being driven into the hole, the coupling element 200 and the locking collar 150 may be rotated and agulated relative to the screw 120, to an angle such that support rod 250 may be properly nested within the channel. In this initial disposition, however, the bottom 251 of the rod 250 seats on the top surface 156 of the locking collar 150 and not fully on the bottom curved surface of the channel.

Referring now to FIG. 9, after the rod 250 has been appropriately positioned, the top locking nut 185 is threaded onto the threading 216 of the upwardly extending members 214a,214b. The lower surface 188 of the nut 185 seats against the top surface 252 of the rod 250. As the nut 185 rotates, and descends relative to the coupling element 200, the rod 250 is driven downward, causing the rod 250 and the locking collar 150 to translate downward slightly. This downward translation causes the tapered side walls 209 of the socket 205 to compress against the locking collar 150, thereby causing the slot 166 to narrow. This radial inward compression causes the head 122 of the screw 120 to be crush locked to the inwardly curved surface 154 of the locking collar 150.

In addition, the rod is locked between the bottom surface 188 of the nut 185 and the top surface 156 of the locking collar 150. This locking prevents the rod 250 from sliding relative to the assembled structure (along an axis which is perpendicular to the plane of FIG. 9). The full insertion of the top locking nut 185, therefore, locks the rod 250 in the channel of the coupling element 200, as well as the screw 120 within the locking collar 150.

Figure 10:
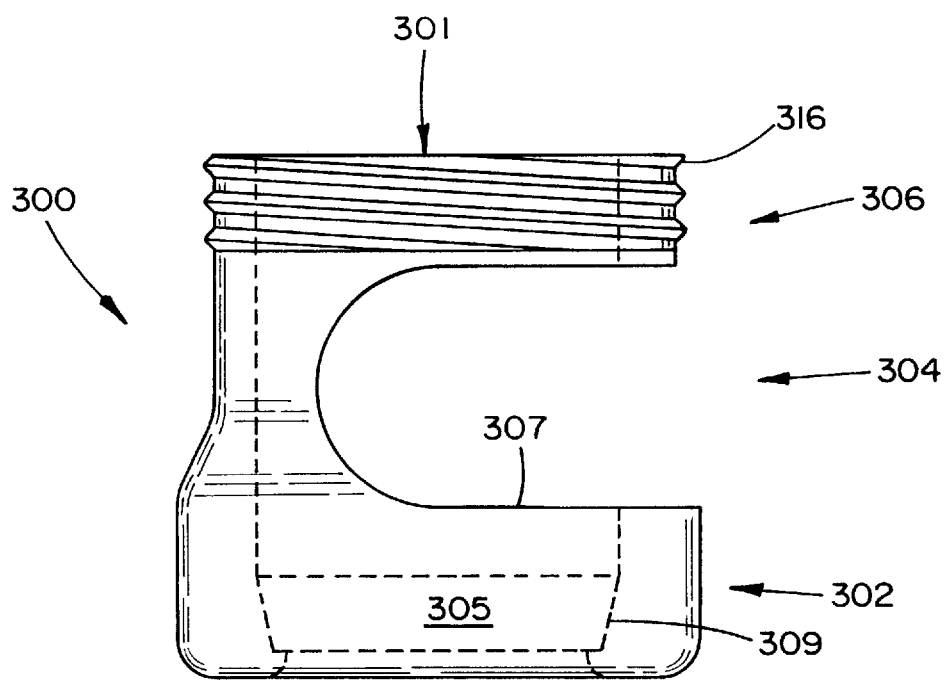
FIG. 10 is a side view of a second coupling element of the present invention having a side loading channel and wherein interior features of the element are shown in phantom.
Figure 11:
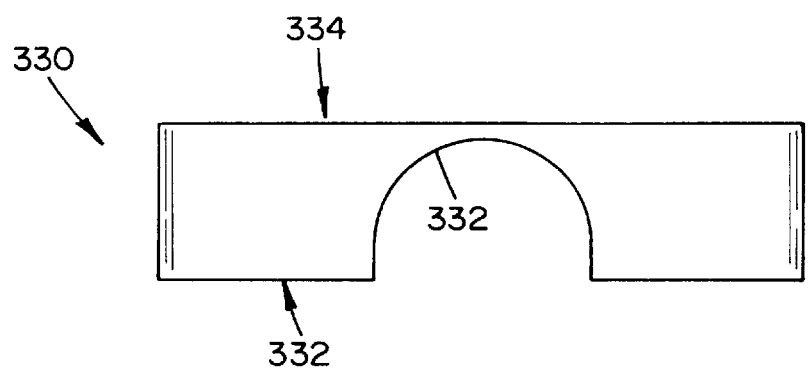
FIG. 11 is a side cross-sectional view of a rod securing sleeve which is utilized with the side loading embodiment of the present invention.
Figure 12:
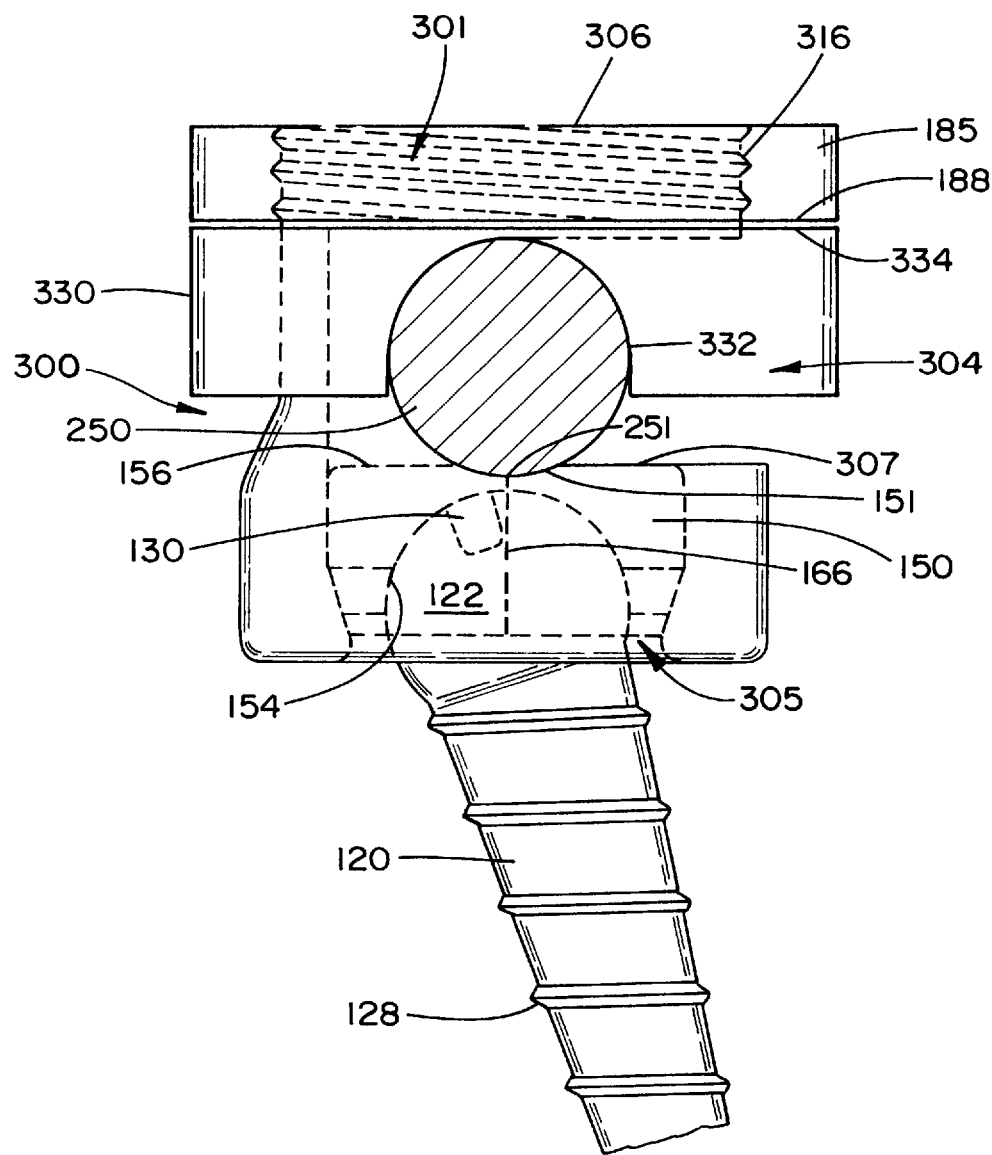
FIG. 12 is a side cross-sectional view of the side loading embodiment of the present invention in its fully assembled disposition having a rod securely locked therein.

Referring now to FIGS. 10, 11, and 12, an alternative, side loading variation of the invention is provided. Referring specifically to FIG. 10, a coupling element 300 having a channel formed in the side thereof is illustrated in a side view, wherein critical features thereof are shown in phantom. This coupling element comprises an axial bore 301 which is similar to the one in the first embodiment, through which the locking collar 150 and the screw 120 may be inserted. The axial bore 301 has an inward taper 309 at the bottom thereof so that the locking collar may initially seat loosely in the socket 305, but may be securely locked therein by the application of a downward force.

The coupling element comprises a lower portion 302, which is similar to the lower portion of the first coupling element 200, as set forth above with respect to FIGS. 6, 8 and 9. The remainder of the coupling element 300 is divided into an intermediate portion 304 and an upper portion 306. The intermediate portion includes the side channel into which the rod 250 is to be secured. In its initial disposition in the socket 305 of the lower portion 302, the top surface 156 of the locking collar 150 extends upwards beyond the lower ledge 307 of the channel. The height of the channel is equal to, or greater than the width of the rod and the extent to which the top surface 156 of the collar 150 rises above the lower ledge 307. This permits the rod 250 to be inserted into the channel and subsequently for it to translate downward therein to force the locking collar 150 downward in the socket 305 (thereby locking it securely therein).

The upper portion 306 of the coupling element 300 comprises a tubular section which includes the top of the axial bore 301, and an exterior threading 316 which is suitable for engagement of either of the top locking nuts set forth with respect to FIGS. 7a and 7b.

Referring to FIG. 11, the rod securing sleeve 330 which is necessary for reliably holding the rod 250 in the channel is shown in a side view. The rod securing sleeve comprises a hollow cylindrical section, having an interior diameter which permits it to be dropped over the upper portion 306 of the coupling element 300, and a lower annular surface 332 which is shaped to cup the rod 250, and prevent its movement. The upper annular surface 334 of the sleeve 330 is suitably flat, so that the lower surface of the top locking nut may seat thereagainst and provide the downward force necessary to lock the entire system together.

Referring now to FIG. 12, in which the fully assembled second embodiment is shown in a side view, the assembly of this embodiment is described. As above, a pre-drilled hole is initially provided in the bone, into which it is desired that the screw 120 be disposed. The hole may be pre-tapped, or the external threading 128 of the screw 120 may include a self-tapping lead edge. In either event, the head 122 of the screw 120 is inserted into the locking collar 150, such that it remains polyaxially free to rotate and angulate relative thereto. The locking collar 150 and the screw 120 are then translated downward, through the axial bore 301 of the coupling element 300, until the locking collar 150 seats loosely in the socket 305 at the tapered bottom of the axial bore 301. At this point in the assembly process, the screw 120 and the locking collar 150 have the capacity to rotate relative to one another, while the loose seating of the locking collar 150 in the socket 305 prevents relative motion of the collar and the element. The top surface 156 of the locking collar 150 is disposed above the lower ledge 307 of the side channel of the intermediate portion 304 of the coupling element 300, such that the notches 151 of the collar 150 are generally aligned with the axis of the channel.

By orienting the locking collar 150 and the screw 120 coaxially, a screwdriving tool may engage the recess 130 in the head 122 of the screw 120 so that it may be driven into the preformed hole in the bone.

Subsequent to the screw 120 being driven into the hole, the coupling element 300 and the locking collar 150 may be rotated and agulated relative to the screw 120, to an angle such that support rod 250 may be properly nested within the side channel. In this initial disposition, however, the bottom 251 of the rod 250 seats on the top surface 156 of the locking collar 150 and not fully on the lower ledge 307 of the channel.

After the rod 250 has been appropriately positioned, a rod securing sleeve 330 is placed over the upper portion 306 of the coupling element 300 and dropped downward so that the bottom annular surface thereof may cup the top of the rod 250. Subsequently, the top locking nut 185 (or 190) is threaded onto the threading 316 until the lower surface 188 thereof seats against the upper annular surface 334 of the sleeve 330. As the nut 185 rotates and descends relative to the coupling element 300, the rod securing sleeve 330 applies a downward force onto the rod 250, which is, in turn, driven downward, causing the rod 250 and the locking collar 150 to translate downward slightly. This downward translation causes the tapered side walls of the socket 305 to compress against the locking collar 150, thereby causing its slot 166 to narrow. This radial inward compression causes the head 122 of the screw 120 to be crush locked to the curved interior surface 154 of the locking collar 150.

In addition, the rod is securely locked between the bottom surface 332 of the rod securing sleeve 330 and the top surface 156 of the locking collar 150. This locking prevents the rod 250 from sliding relative to the assembled structure (along an axis which is perpendicular to the plane of FIG. 12). The full insertion of the top locking nut 185, therefore, locks the rod 250 in the channel of the coupling element 300, as well as the screw 120 within the locking collar 150.

While there has been described and illustrated embodiments of a polyaxial screw and coupling element assembly for use with posterior spinal rod implantation apparatus, it will be apparent to those skilled in the art that variations and modifications are possible without deviating from the broad spirit and principle of the present invention. The present invention shall, therefore, be limited solely by the scope of the claims appended hereto.

We claim:

1. A polyaxial screw and coupling element assembly for use with orthopedic rod implantation apparatus, comprising:
   a polyaxial screw having a semi-spherical head;
   a cylindrical locking collar, having at least one axial slot such that said locking collar may be expanded or contracted by the application of radial forces thereon, a tapered exterior surface, and a semi-spherical interior surface defining a semi-spherical volume in which said semi-spherical head may be initially polyaxially disposed so as to rotate and angulate relative thereto through a range of angles including non-perpendicular angles;
   a coupling element including,
      an axial bore through which said screw may be inserted, said bore having a narrowing tapered bottom portion, said bottom portion forming a socket into which said locking collar may be initially nested so that the screw may remain polyaxially disposed relative to both the locking collar and the coupling element, and said locking collar further being compression lockable in said socket by the application of a downward force thereon such that the taper of the bore applies a radially inward compression force to close the at least one slot and crush lock said semi-spherical interior surface of the locking collar to the semi-spherical head of the screw independent of the relative angulation of the screw to the coupling element and locking collar,
      a rod receiving channel, oriented transverse to said axial bore, in which the rod may be disposed and seated on a top surface of the locking collar, and
      an upper portion having an exterior threading thereon; and
   a top locking nut, mateable with said threading, for locking a rod in said channel and for applying therethrough the downward force necessary to compression lock the locking collar in the bottom socket portion of the axial bore whereby the screw head is crush locked to the interior surface of the locking collar.

2. The assembly as set forth in claim 1, wherein said channel comprises a recess in the side of the coupling element.

3. The assembly as set forth in claim 1, wherein said upper portion comprises a pair of upwardly extending members defining therebetween said channel.

4. The assembly as set forth in claim 1, wherein said tapered exterior surface of said locking collar includes at least one circumferential arc section along a portion of its axial extent which is flat, and wherein said axial bore comprises a corresponding circumferential flat portion such that said locking collar may remain rotationally oriented in said axial bore.

5. The assembly as set forth in claim 1, wherein said top surface of said locking collar comprises a pair of notches for receiving thereon said rod.

6. A orthopedic rod implantation apparatus having polyaxial screw and coupling elements, comprising:
   at least one elongate rod;
   a plurality of rod coupling assemblies, wherein at least one of said assemblies comprises,
      a polyaxial screw having a semi-spherical head;
      a cylindrical locking collar, having at least one axial slot such that said locking collar may be expanded or contracted by the application of radial forces thereon, a tapered exterior surface, and a semi-spherical interior surface defining a semi-spherical volume in which said semi-spherical head may be initially polyaxially disposed so as to rotate and angulate relative thereto through a range of angles including non-perpendicular angles;
      a coupling element including,
         an axial bore through which said screw may be inserted, said bore having a narrowing tapered bottom portion, said bottom portion forming a socket into which said locking collar may be initially nested so that the screw may remain polyaxially disposed relative to both the locking collar and the coupling element, and said locking collar further being compression lockable in said socket by the application of a downward force thereon such that the taper of the bore applies a radially inward compression force to close the at least one slot and crush lock said semi-spherical interior surface of the locking collar to the semi-spherical head of the screw independent of the relative angulation of the screw to the coupling element and locking collar,
         a rod receiving channel, oriented transverse to said axial bore, in which the rod may be disposed and seated on a top surface of the locking collar, and
         an upper portion having an exterior threading thereon; and
      a top locking nut, mateable with said threading, for locking a rod in said channel and for applying therethrough the downward force necessary to compression lock the locking collar in the bottom socket portion of the axial bore whereby the screw head is crush locked to the interior surface of the locking collar.

7. The assembly as set forth in claim 6 wherein said channel comprises a recess in the side of the coupling element.

8. The assembly as set forth in claim 6, wherein said upper portion comprises a pair of upwardly extending members defining therebetween said channel.

9. The assembly as set forth in claim 6, wherein said tapered exterior surface of said locking collar includes at least one circumferential arc section along a portion of its axial extent which is flat, and wherein said axial bore comprises a corresponding circumferential flat portion such that said locking collar may remain rotationally oriented in said axial bore.

10. The assembly as set forth in claim 6, wherein said top surface of said locking collar comprises a pair of notches for receiving thereon said rod.

* * * * *